United States Patent
Lafferty et al.

(10) Patent No.: US 6,918,738 B2
(45) Date of Patent: Jul. 19, 2005

(54) STACKABLE SAMPLE HOLDING PLATE WITH ROBOT REMOVABLE LID

(75) Inventors: William Michael Lafferty, Encinitas, CA (US); Scott Wayne Beaver, San Diego, CA (US); Charles Wilson Tweedy, San Diego, CA (US)

(73) Assignee: Diversa Corporation, San Diego, CA (US)

(*) Notice: Subject to any disclaimer, the term of this patent is extended or adjusted under 35 U.S.C. 154(b) by 145 days.

(21) Appl. No.: 10/095,906

(22) Filed: Mar. 11, 2002

(65) Prior Publication Data
US 2003/0168458 A1 Sep. 11, 2003

(51) Int. Cl.[7] .......................... B65G 59/06; B65H 3/00; C12M 1/22; C12M 3/00; C12M 1/34
(52) U.S. Cl. .................. 414/797.7; 435/305.1; 435/305.3; 435/288.4
(58) Field of Search ................ 414/797.7; 211/13.1, 211/41.11, 85.13; 206/558, 562; 435/288.3, 288.4, 305.1, 305.2, 305.3, 305.4

(56) References Cited

U.S. PATENT DOCUMENTS

| | | | |
|---|---|---|---|
| D202,700 S | 11/1965 | Cooke | |
| 3,556,731 A | 1/1971 | Martin | |
| 3,634,651 A | 1/1972 | Siegel | |
| 3,649,464 A | 3/1972 | Freeman | |
| D246,466 S | 11/1977 | Attree | |
| 4,154,795 A | 5/1979 | Thorne | |
| 4,299,796 A | 11/1981 | Hogen Esch | |
| D283,162 S | 3/1986 | Godsey | |
| D284,699 S | 7/1986 | Jolley | |
| 4,599,315 A | 7/1986 | Terasaki | |
| 4,673,651 A * | 6/1987 | Rothenberg et al. | 435/305.2 |
| 4,682,891 A | 7/1987 | de Macario | |
| 4,704,255 A | 11/1987 | Jolley | |
| 4,710,031 A | 12/1987 | Kelly | |
| 4,735,778 A | 4/1988 | Maruyama | |
| 4,786,601 A * | 11/1988 | Rothenberg | 435/305.2 |
| 4,824,791 A | 4/1989 | Ekholm | |
| D302,207 S | 7/1989 | Matkovich | |
| D303,149 S | 8/1989 | Andersen | |
| 4,919,894 A | 4/1990 | Daniel | |
| 5,073,346 A | 12/1991 | Partanen | |
| 5,096,672 A | 3/1992 | Tervamaki | |
| 5,213,505 A | 5/1993 | Laipply | |
| 5,843,767 A | 12/1998 | Beattie | |
| 5,961,926 A * | 10/1999 | Kolb et al. | 435/305.2 |
| 6,027,873 A | 2/2000 | Schellenberger | |
| 6,306,578 B1 | 10/2001 | Schellenberger | |
| 6,340,589 B1 * | 1/2002 | Turner et al. | 435/305.2 |
| 6,426,215 B1 * | 7/2002 | Sandell | 435/305.3 |

FOREIGN PATENT DOCUMENTS

WO    WO 99/34920    7/1999

* cited by examiner

*Primary Examiner*—Gene O. Crawford
(74) *Attorney, Agent, or Firm*—Nydegger & Associates

(57) ABSTRACT

A holding plate includes a flat base member with a surface that is formed with a plurality of stations (wells or depressions) for holding specimens. A panel extends downwardly from the edge of the surface to create a concavity for receiving a lid member therein. The panel also has a flange extending outwardly from the concavity. The flat lid member has a skirt with a rim that extends from the edge of the lid member to create a hollow for receiving a base member therein. In operation, a robot or mechanical device selectively engages the flange of the base member and the rim of the lid member to engage or disengage the base and lid members. This allows for individual movement of either the base member or the lid member. This also allows for collective movement of the engaged base and lid members for stacking and storage.

12 Claims, 2 Drawing Sheets

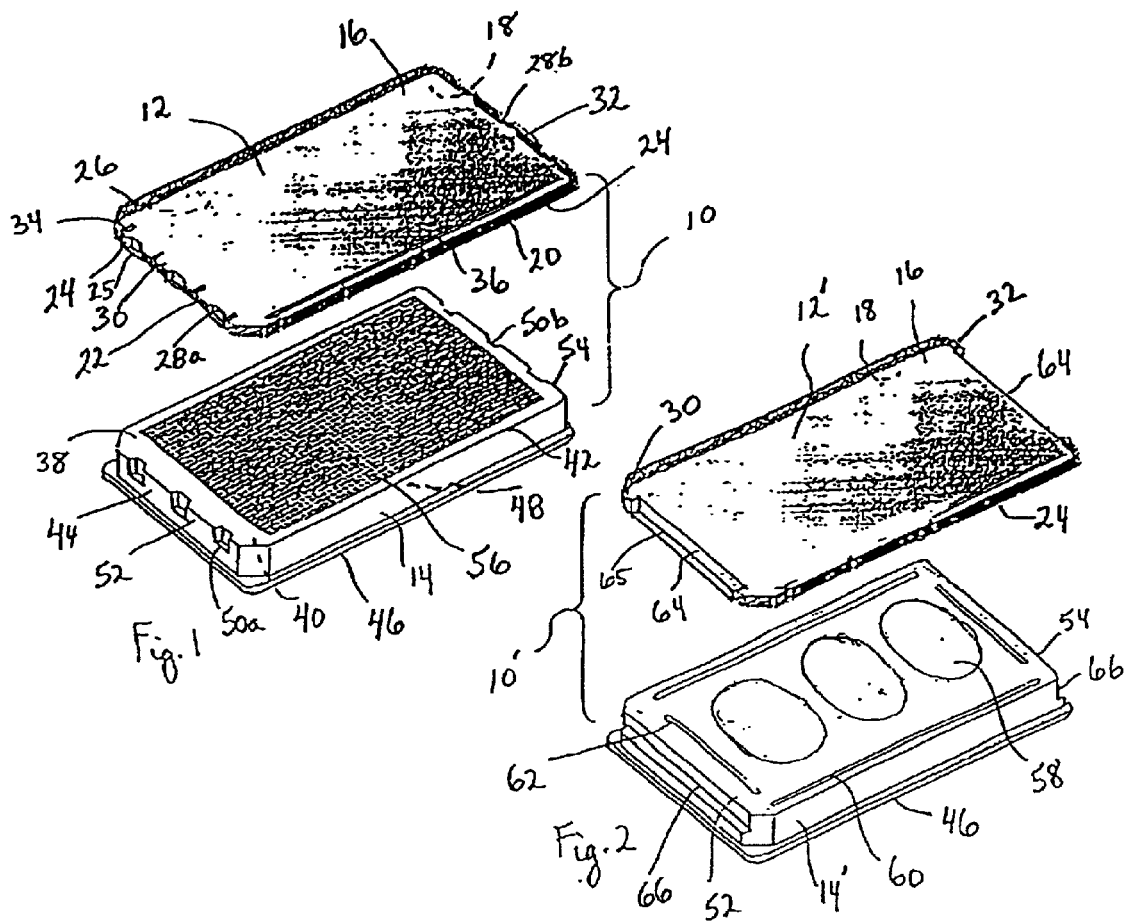
Fig. 1
Fig. 2
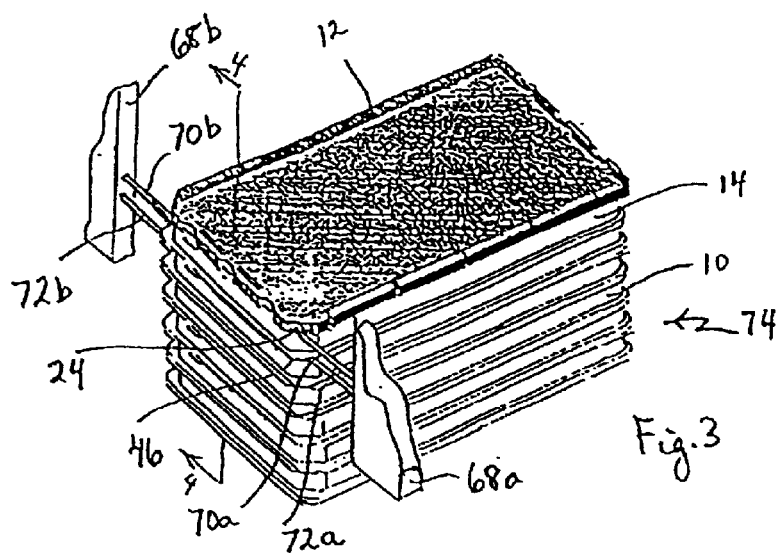
Fig. 3

STACKABLE SAMPLE HOLDING PLATE WITH ROBOT REMOVABLE LID

FIELD OF THE INVENTION

The present invention pertains generally to specimen holding trays. More particularly, the present invention pertains to holding trays that have lids which can be selectively removed from or engaged with the tray for protecting specimen samples held on the tray. The present invention is particularly, but not exclusively, useful as a holding tray that can be robotically manipulated and transferred by mechanical devices from one location to another, with or without its lid, for purposes of processing sample specimens held on the tray and for stacking the trays and lids during storage of the specimen samples.

BACKGROUND OF THE INVENTION

The transfer or movement of a large number of separate specimen samples for processing purposes requires a consideration of several factors. In particular, when viable specimens are involved, these considerations include protection of the carrier medium in which the specimens are suspended (e.g. agar or fluid solution), the nature of samples and their size. Additional considerations involve protection of the specimen samples during processing and storage, as well as the facility with which the samples can be moved from one location to another.

For many different reasons, it may be desirable to employ robots or other mechanical devices for the purpose of moving, handling and transferring sample specimens. Importantly, if used, robotic or mechanical devices must be able to function reliably, and to effectively interact with whatever tray, plate, container or other holding device that is being used for holding and transporting the specimen samples. More specifically, when the particular holding device also includes a lid member that needs to be selectively engaged and disengaged with a base member that is holding a specimen sample, the robot or mechanical device needs to be capable of performing such operational functions. In any event, it is very desirable that the robot, or mechanical device, be simultaneously functional with many holding plates to create a high operational throughput capability for the specimen sample processing system.

In light of the above, it is an object of the present invention to provide a holding plate (or tray) that can be manipulated and moved by a robot or some similar mechanical device. Another object of the present invention is to provide a holding plate which has a lid for protecting specimen samples when they are held on the plate, wherein the plate and its lid can be collectively or individually manipulated by a robot or some similar mechanical device. Still another object of the present invention is to provide a holding plate that is stackable with similar type holding plates, along with a method for stacking these plates which effectively increases the throughput of sample specimens in a specimen processing system. Yet another object of the present invention is to provide a holding plate, and a method for stacking them, that is easy to use, relatively simple to manufacture and comparatively cost effective.

SUMMARY OF THE PREFERRED EMBODIMENTS

A holding plate (microtiter plate or tray) in accordance with the present invention is adapted for use in a stacking system that requires the selective movement of individual plates. More specifically, the plate of the present invention includes a base member having wells for holding agar specimens or specimens in a fluid solution. As an alternative to wells, the holding plate of the present invention can be formed with depressions that function as stations for holding the specimens. In either case, it also has a lid member that covers the specimens in the wells to protect them from contamination. An important aspect of the present invention is that the lid member and the base member can be selectively engaged with each other, and disengaged from each other, by a mechanical system. Specifically, the mechanical system can remove either the base member or the lid member. Also, the mechanical system can stack integrated holding plates (i.e. holding plates wherein the lid member is engaged with the base member) with other integrated holding plates. Further, the present invention provides for the movement and manipulation of uncovered specimens in the wells of the base member while the lid member is disengaged from the base member. On the other hand, the movement and stacking of covered specimens can also be accomplished when the lid member is engaged with the base member.

In detail, the holding plate of the present invention includes a base member having a substantially flat, rectangular shaped surface that is formed with a plurality of wells. Typically, in accordance with industry specifications, there may be a variety of sizes and number of wells in each holding plate. For example, the holding tray can have a commonly used well configuration such as one wherein there are either 96, 384 or 1536 wells that are formed into the surface of the base member. Further for the present invention, a panel, which is formed as part of the base member, extends downwardly from its surface to form a concavity in the base member that is immediately below the wells. Also, the panel of the base member is formed with at least one recess, or keyway, that is located at the edge of the base member. In addition to the other mentioned features, the panel is formed with a flange that extends outwardly from the panel, away from the concavity. The specific purpose of this flange is to provide a means by which the mechanical system (e.g. robot) can effectively grip or support the base member.

In addition to the base member mentioned above, the microtiter plate of the present invention includes a lid member for covering the wells that are formed into the base member. More specifically, the lid member is formed with a substantially flat surface for covering the wells of the base member, and it includes a skirt that extends downwardly from the peripheral edge of its flat surface to create a hollow therewith. Further, this skirt is formed with at least one indentation (key) that is dimensioned for a mating engagement with a respective recess (keyway) of the base member. Additionally, the skirt of the lid member is formed with a rim at the margin of the skirt to provide a means by which the mechanical system (e.g. robot) can effectively grip or support the lid member. Also, the skirt is formed with a lip that extends outwardly from the rim. The specific purpose of this lip is to provide a means by which the mechanical means can lift the lid member from the base member when the lid member is engaged with the base member.

An additional feature of the microtiter plate of the present invention is that either the lid member or the base member can include at least one exterior rib and at least one interior rib. More specifically, in the case of the lid member, the exterior ribs are formed to distance it from a base member whenever the lid member is received into the concavity of a base member. Similarly, the plurality of interior ribs are formed on the lid member to distance it from a base member whenever a base member is inserted into the hollow of the lid member to cover the wells of the base member with the lid member. In effect, the ribs on the lid member facilitate engagements and disengagements of the lid member with a base member, and they enhance the stability of their combination when engaged. The substantially same result is obtained when the interior and exterior ribs are formed on the base member.

In the operation of the present invention, a mechanical system, such as a robot or an automated stacking machine, is used to simultaneously support the flange of the base member and the rim of the lid member. Alternatively, the mechanical means can separately support either the base member or the lid member. By way of example, the mechanical means can allow the base member to be withdrawn from the hollow of the lid member to disengage the base member from the lid member. This can be done by supporting the base member during separation, or by simply allowing the base member to fall from the lid member. The separated base member can then be moved away from the lid member by any known means to manipulate specimens in the wells as desired.

Once the manipulation of specimens in the wells of an uncovered base member has been completed, the base member is returned to the lid member for reinsertion into the hollow of the lid member. Subsequently, the mechanical means can be used to hold the lid member on the base member, to thereby maintain the integrity for the holding plate while it is being transferred to another location. Upon arriving at the location, the integrated holding plate (i.e. a holding plate wherein the base member is engaged with a lid member) can be stacked with other holding plates in either of two ways. For one, the lid member of the integrated holding plate can be selectively inserted into the concavity of a base member of another holding plate. Alternatively, the base member of the integrated holding plate can receive the lid member of another holding plate into its concavity.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is an exploded perspective view of a holding plate and its lid in accordance with the present invention;

FIG. 2 is an exploded perspective view of an alternate embodiment of a holding plate and its lid in accordance with the present invention;

FIG. 3 is a perspective view of a plurality of holding plates in a stacked condition;

DESCRIPTION OF THE PREFERRED EMBODIMENT

Figure 4A:
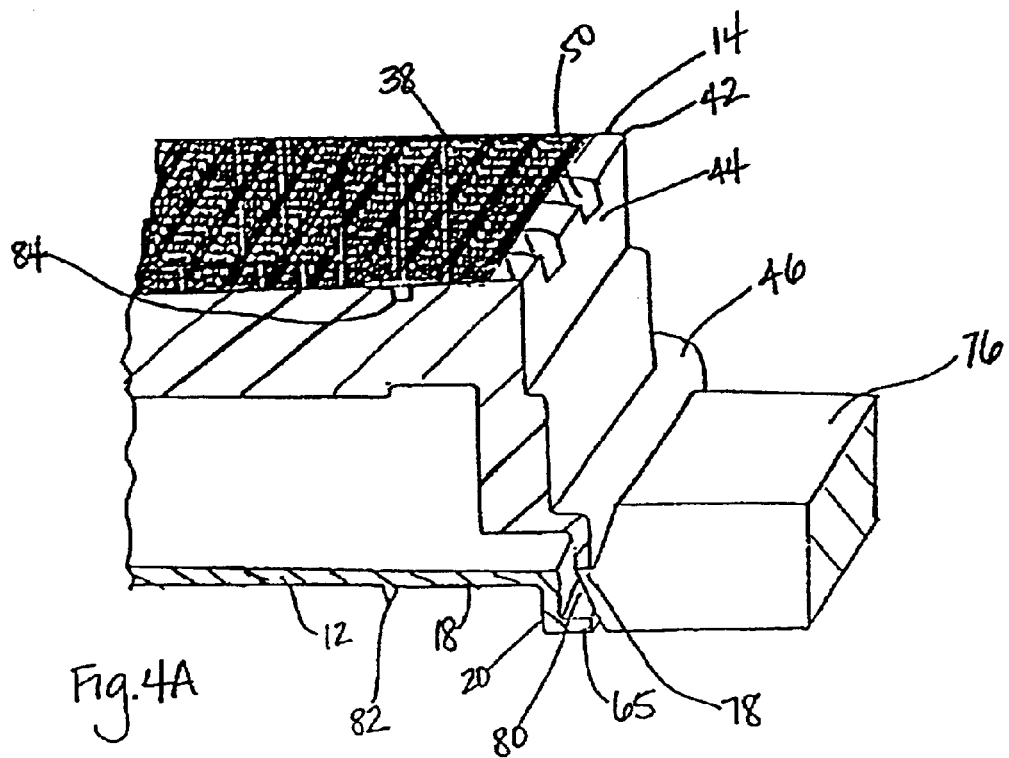
FIG. 4A is a cross-sectional view of a robot engaged with a base member as would be seen along the lines 4—4 in FIG. 3.

Referring initially to FIG. 1, a holding plate in accordance with the present invention is shown and is designated 10. As shown, the holding plate 10 includes a lid member 12 and a base member 14. In general, for the purposes of the present invention, the holding plate 10 can be variously referred to as a tray, a microtiter plate, a GigaMatrix™ plate, a petri dish, or any other type container well known in the pertinent art for holding specimen samples.

Still referring to FIG. 1, in detail, the lid member 12 is shown to have a first (upper) surface 16 and an opposite second (lower) surface 18. Both of these surfaces 16, 18 are substantially flat, and the lid member 12 has a skirt 20 that extends downwardly from the edge 22 that borders the surfaces 16, 18. Importantly, the skirt 20 terminates with a rim 24 having a lip 25 which extends outwardly from the rim 24. In more detail, the lip 25 lies in a plane that is substantially parallel to the first surface 16. With this construction, the skirt 20 effectively surrounds the second (lower) surface 18 of the lid member 12 to define a hollow 26 that is located between the rim 24 of skirt 20 and the second surface 18. FIG. 1 also shows that the lid member 12 is formed with indentations 28, of which the indentation 28a (located at end 30 of lid member 12) and the indentation 28b (located at end 32 of lid member 12) are only exemplary. Additionally, FIG. 1 also shows that the lid member 12 is formed with a rib 34 (shown at end 30), and a rib 36 (extending between ends 30 and 32). As intended for the holding plate 10 of the present invention, a plurality of similar ribs 34 can be formed at both ends 30 and 32 and a plurality of similar ribs 36 can be formed between the ends 30 and 32. Further, the ribs 34 and 36 can be formed on both the first surface 16 and on the second surface 18 of the lid member 12.

The structural detail of base member 14 is perhaps best appreciated with reference to FIG. 1, wherein it is shown that the base member 14 has a first (upper) surface 38 and an opposite second (lower) surface 40, both of which are substantially flat. The first and second surfaces 38, 40 terminate at an edge 42 and a panel 44 extends downwardly from the edge 42. Importantly, the panel 44 terminates with a flange 46 that helps define a concavity 48 between the flange 46 and the second (lower) surface 40 of the base member 14. For the present invention, the flange 46 is oriented substantially parallel to the second surface 40 and it extends outwardly and away from the concavity 48.

Still considering the base member 14, it will be seen in FIG. 1 that it is formed with a plurality of recesses 50, of which the recess 50a at end 52 and the recess 50b at end 54 are only exemplary. Insofar as the relationship between the lid member 12 and the base member 14 is concerned, it is to be appreciated that the hollow 26 of lid member 12 is dimensioned to receive the first surface 38 of base member 14 therein. With this engagement, the first surface 38 of base member 14 is juxtaposed with the second surface 18 of the lid member 12. Due to the ribs 34, 36 on the second surface 18 of lid member 12, however, there will be a slight distance separating the surfaces 38 and 18. As intended for the present invention, this cooperation between the lid member 12 and the base member 14 facilitates their engagement and disengagement. Further, upon engagement of the lid member 12 with the base member 14, it will be appreciated that the indentations 28a and 28b of lid member 12 will mate with respective recesses 50a and 50b of the base member 14. This cooperation between indentations 28 (keys, keyways)

and respective recesses 50 (keyways, keys) will also facilitate the engagement and disengagement of the lid members 12 with the base members 14 that are located either above or below the lid member 12.

For the holding plate 10 of the present invention, it is important to appreciate the interactive aspects of the lid member 12 and the base member 14. Specifically, similar to the interaction between the base member 14 and the hollow 26 of the lid member 12, the concavity 48 of the base member 14 is dimensioned to receive a lid member 12 therein. With this engagement, the first surface 16 of a lid member 12 is juxtaposed with the second surface 40 of the base member 14. Again, due to the ribs 34, 36 on the first surface 16 of lid member 12, there will be a slight distance separating the surfaces 40 and 16. As before, this cooperation between the lid member 12 and the base member 14 is intended to facilitate their engagement and disengagement.

As indicated above, the intended function of the holding plate 10 is to hold specimen samples (not shown). For this purpose, first surface 38 of base member 14 can be formed with a plurality of stations, such as wells 56 that can be of any size and shape well known in the pertinent art. Specifically, these stations or wells 56 can be through-hole wells of a type which allow the wells 56 to be filled with a fluid solution as a result of a wicking action. Alternatively, the first surface 38 of base member 14 can be formed with depressions 58, as shown in FIG. 2. In which case, the stations can be filled with either agar or a fluid solution.

Several alternative features for the present invention can be appreciated by considering the holding plate 10' shown in FIG. 2. For one alternative feature, instead of using ribs 34, 36 on lid member 12, the base member 14 can be formed with a plurality of ribs 60 that extend between the ends 52, 54 of base member 14, and a plurality of ribs 62 at the respective ends 52, 54. Similar to the ribs 34, 36 on lid member 12, the ribs 60, 62 on base member 14 can be formed on both its first surface 38 and its second surface 40. Regardless whether ribs 34, 36 on lid member 12 are used, or ribs 60, 62 on base member 14 are used, the intended function is the same.

Still referring to FIG. 2, another alternative feature for the present invention concerns the engagement and disengagement of the lid member 12' with the base member 14'. Specifically, as shown in FIG. 2, the lid member 12' is formed with elongated indentations 64 that effectively span the respective ends 30, 32. Extending outwardly from the elongated indentations 64 is an elongated lip 65 which lies in a plane that is substantially parallel to the first surface 16 of the lid member 12'. As shown in FIG. 2, the base member 14' has compatible recesses 66 that are elongated for mating engagement with the indentations 64. As before with the indentations 28 and recesses 50 of holding plate 10, the functional purpose of the indentations 64 and recesses 66 is to facilitate the engagement and disengagement of lid members 12' with base members 14' that are located either above or below the lid member 12'.

Figure 4B:
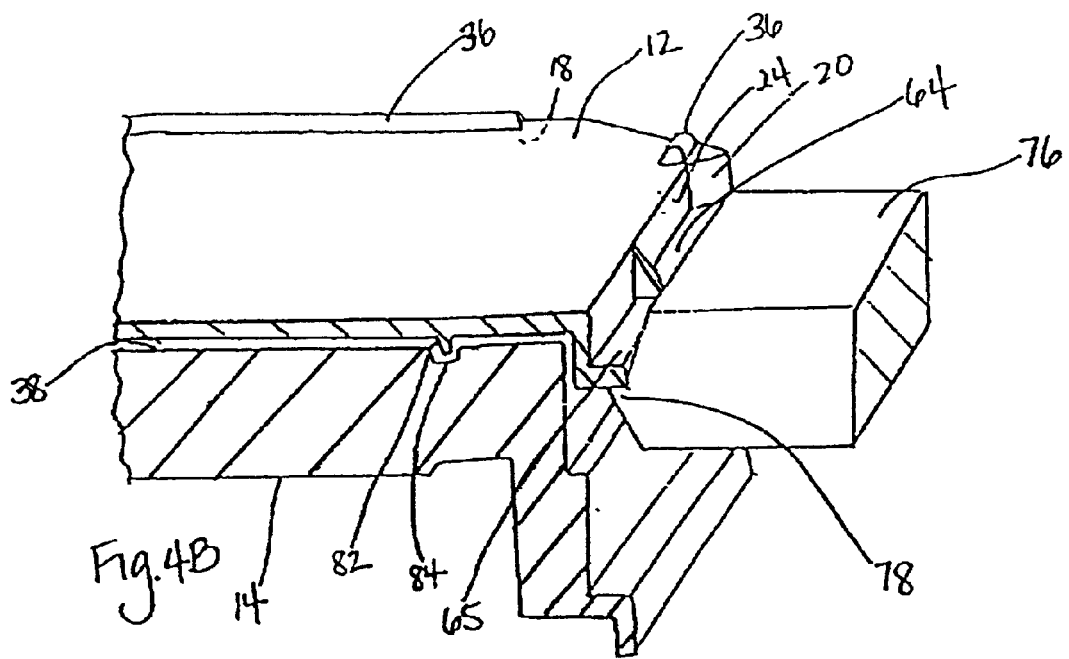
FIG. 4B is a cross-sectional view of a robot engaged with a lid member as seen from the same perspective as FIG. 4A.

Another alternative feature for the present invention can be seen in FIGS. 4A and 4B. Specifically, the lid member 12 can be formed with a protrusion 82, extending away from the second surface 18 of the lid member 12. As also shown, the base member 14 can be formed with a compatible niche 84 on its first surface 38 for a mating engagement with the protrusion 82 of the lid member 12. With the insertion of the protrusion 82 into the niche 84, the lid member 12 can be effectively stabilized on the base member 14 whenever the lid member 12 is positioned over the base member 14. Optionally, the niche 84 can be eliminated. In any event, the protrusions 82 are positioned to act as a vapor barrier that will reduce air circulation over the first (upper) surface 38 of the base member 14 and, thereby, minimize evaporation from the wells 56 of the base member 14. Preferably, in order to allow some air exchange in the wells 56, the protrusion 82 is not in direct contact with the surface 38, or with the niche 84.

The functional operation of the holding plates 10 of the present invention may be best appreciated by reference to FIGS. 3, 4A and 4B. It will be appreciated that the holding plates 10 can be manipulated by a robot, or some other similar mechanical device, with actuators 68 that are engageable with the holding plate 10. In FIG. 3, a mechanical device having actuators 68a and 68b are shown to be exemplary of any mechanical device well known in the art that is capable of accomplishing the functions disclosed herein. An alternative mechanical device can been seen in FIGS. 4A and 4B.

Referring back to FIG. 3, the actuators 68a and 68b are shown with respective first supports 70a and 70b and respective second supports 72a and 72b. It will be appreciated, however, that only one set of supports (i.e. 70a,b or 72a,b) may be employed with slight modifications in procedures.

In operation, as shown in FIG. 3, the first supports 70a and 70b of respective actuators 68a and 68b can be selectively positioned for contact with the lip 25 of a lid member 12. Similarly, the second supports 72a and 72b of the respective actuators 68a and 68b can be selectively positioned for contact with the flange 46 of a base member 14. As indicated above, however, it is possible that only one set of supports (70 or 72) are operated to contact either lip 25 or flange 46. In any event, by using the effects of gravitational acceleration, the supports 70 and/or 72 of an actuator 68 can be extended or withdrawn to manipulate an individual holding plate 10 (or 10') or a plurality of holding plates (e.g. stack 74 shown in FIG. 3). Specifically, by engaging the flange 46 of a base member 14 (e.g. with second supports 72a,b), the actuator 68 can lift the base member 14 along with all of the holding plates 10 above it. Alternatively, with this same engagement, the actuator 68 can allow the unsupported lid member 12 below the supported base member 14 to fall, along with all of the holding plates 10 below it, by the effect of gravity. Either way, the lid member 12 of the lower holding plate 10 is separated from the supported base member 14 of the upper holding plate 10. Similarly, by engaging the lip 25 of a lid member 12, the actuator 68 can either lift the lid member 12 along with all of the holding plates 10 above it, or allow the base member 14 and all of the holding plates 10 below it to fall by the effect of gravity.

FIGS. 4A and 4B show an actuator 76 of the alternative mechanical device having a supporter 78 shown engaged with the base member 14 in FIG. 4A, and with the lid member 12 in FIG. 4B. Specifically, in FIG. 4A, the supporter 78 can be selectively positioned through an opening 80 between the flange 46 of the base member 14 and the lip 65 of the lid member 12. Importantly, this opening 80 allows for the supporter 78 to lift the flange 46 away from the lip 65 of the lid member 12. By doing this, the actuator 76 can lift the base member 14 along with all of the holding plates 10 above it.

As shown in FIG. 4B, the supporter 78 of the actuator 76 can be selectively positioned for contact with the lip 65 of the lid member 12. For this engagement, the supporter 78 can be positioned beneath the lip 65 to lift the lid member 12 away from the base member 14.

By using the actuators 68 of a robot or some other mechanical means to manipulate the holding plates 10 of the present invention as disclosed above, it is intended for the present invention that individual base members 14 will be moved or transferred to process specimen samples that are held in the stations (i.e. wells 56 or depressions 58) of the base member 14. Before doing this, however, the present invention contemplates removing a lid member 12 from the base member 14. Subsequently, after the sample specimens (not shown) have been processed, the present invention contemplates mechanically repositioning a lid member 12 over the base member 14 to protect the specimen samples. Further, the holding plates 10 can be handled individually or collectively, in stacks 74.

While the particular Stackable Sample Holding Plate with Robot Removable Lid as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A holding plate for use in a stacking system which comprises:

a substantially flat base member having a first surface and a second surface with a peripheral edge therebetween, wherein said first surface is substantially flat and is formed with a plurality of stations for holding specimens on said plate, and further wherein said peripheral edge is formed with a recess;

a panel extending from said peripheral edge of said base member substantially perpendicular to said second surface thereof to border said second surface and create a concavity therewith, wherein said panel is formed with a flange extending outwardly from said concavity and substantially parallel to said second surface of said base member for selective use by said system in supporting said base member;

a substantially flat lid member having a first surface and a second surface with an edge therebetween; and a skirt extending from said edge of said lid member substantially perpendicular to said second surface thereof to surround said second surface and create a hollow therewith, wherein said skirt is formed with an indentation for mating engagement with said recess of said base member when said second surface of said lid member is positioned over said first surface of said base member to cover said plurality of wells, and further wherein said skirt is formed with a rim having a lip extending outwardly from said rim for selective use by said system in supporting said lid member.

2. A holding plate as recited in claim 1 wherein said stations are wells.

3. A holding plate as recited in claim 1 wherein said stations are wells with each said well having a fluid volume greater than approximately five microliters.

4. A holding plate as recited in claim 1 wherein said system is a robot.

5. A holding plate as recited in claim 1 wherein said system is an automated plate stacking machine.

6. A holding plate as recited in claim 1 further comprising:

a plurality of said base members; and a plurality of said lid members wherein said lid members are engaged with said base members to form respective said integrated holding plates, and further wherein one said integrated holding plate is stacked on another said integrated holding plate.

7. A holding plate as recited in claim 1 further comprising a means for establishing a vapor barrier between said base member and said lid member during a mating engagement therebetween, when said base member and said lid member are engaged to form an integrated holding plate.

8. A holding plate as recited in claim 1 wherein said base member and said lid member are substantially rectangular with respective first and second parallel ends, with said ends being distanced from each other by respective first and second parallel sides.

9. A holding plate as recited in claim 8 wherein one said recess is formed at said first end of said base member and another said recess is formed at said second end of said base member, and further wherein one said indentation is formed at said first end of said lid member and another said indentation is formed at said second end of said lid member to conform said indentations of said lid member with respective recesses of said base member.

10. A holding plate as recited in claim 1 wherein said base member is insertable into said hollow of said lid member, and wherein said lid member is insertable into said concavity of said base member.

11. A holding plate as recited in claim 10 wherein said lid member further comprises:

a plurality of interior ribs formed on said second surface of said lid member to distance said second surface thereof from said first surface of one said base member when said base member is received into said hollow of said lid member to cover said plurality of stations; and a plurality of exterior ribs formed on said first surface of said lid member to distance said first surface thereof from said second surface of one said base member when said lid member is received in said concavity of said base member.

12. A holding plate as recited in claim 10 wherein said base member further comprises:

a plurality of interior ribs formed on said second surface of said base member to distance said second surface thereof from said first surface of one said lid member when said lid member is received into said concavity of said base member; and a plurality of exterior ribs formed on said first surface of said base member to distance said first surface thereof from said second surface of one said lid member when said base member is received in said hollow of said lid member to cover said plurality of stations.

* * * * *